(12) United States Patent
Meiere et al.

(10) Patent No.: US 7,238,821 B2
(45) Date of Patent: Jul. 3, 2007

(54) METHOD FOR LARGE SCALE PRODUCTION OF ORGANOMETALLIC COMPOUNDS

(75) Inventors: Scott Houston Meiere, Williamsville, NY (US); David Walter Peters, North Tonawanda, NY (US)

(73) Assignee: Praxair Technology, Inc., Danbury, CT (US)

( * ) Notice: Subject to any disclaimer, the term of this patent is extended or adjusted under 35 U.S.C. 154(b) by 321 days.

(21) Appl. No.: 10/678,074

(22) Filed: Oct. 6, 2003

(65) Prior Publication Data

US 2005/0075510 A1 Apr. 7, 2005

(51) Int. Cl.
*C07F 7/00* (2006.01)
*C07F 11/00* (2006.01)
*C07F 17/00* (2006.01)

(52) U.S. Cl. ............................ 556/51; 556/42; 556/43; 556/52; 556/57; 556/58

(58) Field of Classification Search .................. 556/42, 556/43, 51, 52, 57, 58
See application file for complete search history.

(56) References Cited

U.S. PATENT DOCUMENTS

| | | | |
|---|---|---|---|
| 6,175,027 B1 | 1/2001 | Sullivan et al. | 556/153 |
| 6,420,583 B1 | 7/2002 | Lienhard et al. | 556/136 |
| 6,521,772 B1 | 2/2003 | Lienhard et al. | 556/136 |

OTHER PUBLICATIONS

Balboni et al., Inorganic Chemistry, vol. 40, No. 26, pp. 6588-6597 (2001).*

Hausmann, Dennis M.. et al., "Atomic Layer Deposition of Hafnium and Zirconium Oxides Using Metal Amide Precursors", *American Chemical Society*, Chem. Mater. 2002, 14, 4350-4358.

Gary M. Diamond, et al., "Synthesis of Group 4 Metal rac-(EBI)M(NR$_2$)$_2$ Complexes by Amine Elimination. Scope and Limitations". *American Chemical Society*, Organometallics 1996, 15, 4030-4037.

Gary M. Diamond, et al.. "Efficient Synthesis of Chiral ansa-Metallocenes by Amine Elimination. Synthesis, Structure, and Reactivity of rac-(EBI)Zr(Nme$_2$)$_2$", *American Chemical Society*, J. Am. Chem. Soc. 1996, 118, 8024-8033.

Malcolm H. Chisholm, et al., "Tetrakisdimethylamidozirconium and Its Dimethylamido Lithium Adduct: Structures of IZr(Nme$_2$)$_6$Li$_2$(THF)"Polyhedron vol. 7, No. 24, pp. 2515-2520, 1988.

* cited by examiner

*Primary Examiner*—Porfirio Nazario-Gonzalez
(74) *Attorney, Agent, or Firm*—Gerald L. Coon

(57) ABSTRACT

This invention relates to a one pot method for large scale production of an organometallic compound comprising (i) reacting a hydrocarbon or heteroatom-containing material with a base material in the presence of a solvent and under reaction conditions sufficient to produce a first reaction mixture comprising a hydrocarbon or heteroatom-containing compound, (ii) adding a metal source compound to said first reaction mixture, (iii) reacting said hydrocarbon or heteroatom-containing compound with said metal source compound under reaction conditions sufficient to produce a second reaction mixture comprising said organometallic compound, and (iv) separating said organometallic compound from said second reaction mixture.

63 Claims, No Drawings

METHOD FOR LARGE SCALE PRODUCTION OF ORGANOMETALLIC COMPOUNDS

FIELD OF THE INVENTION

This invention relates to a one pot method for the large scale production of organometallic compounds, a process for producing a film, coating or powder from the organometallic compounds, and to certain hydrocarbon or heteroatom-containing compounds and organometallic compounds.

BACKGROUND OF THE INVENTION

Chemical vapor deposition methods are employed to form films of material on substrates such as wafers or other surfaces during the manufacture or processing of semiconductors. In chemical vapor deposition, a chemical vapor deposition precursor, also known as a chemical vapor deposition organometallic compound, is decomposed thermally, chemically, photochemically or by plasma activation, to form a thin film having a desired composition. For instance, a chemical vapor deposition organometallic precursor can be contacted with a substrate that is heated to a temperature higher than the decomposition temperature of the precursor, to form a metal or metal oxide film on the substrate.

Preferably, chemical vapor deposition organometallic precursors are volatile, heat decomposable and capable of producing uniform films under chemical vapor deposition conditions. In producing thin films by chemical vapor deposition processes, precursors that are liquid at room temperature, rather than solids, often are preferred.

The synthetic process utilized to generate the desired organometallic precursors is highly important, and must insure high purity, thoughput, and consistency. However, the air-sensitive nature of the starting materials and the final product make the synthesis of organometallic precursors more challenging. When starting materials are solids, it makes air-free transfer more difficult. Simply storing the starting materials can be problematic, and purity levels from commercial sources are rarely greater than 95% (which creates potential loses in yield and final product purity). Furthermore, filtering of the reaction must be performed in an inert atmosphere which presents another challenge. Therefore, developing a methodology for producing organometallic precursors that addresses the aforementioned potential hold-ups would be beneficial toward establishing the large scale production of these materials for use in the electronics industry.

Further, in developing methods for forming thin films by chemical vapor deposition methods, a need continues to exist for chemical vapor deposition organometallic precursors that preferably are liquid at room temperature, have relatively high vapor pressure and can form uniform films. A need continues to exist for developing new compounds and for exploring their potential as chemical vapor deposition precursors for film depositions. It would therefore be desirable in the art to provide a chemical vapor deposition precursor in liquid form and producable on a large scale with high yields. Further, it would be a significant advancement in the art to synthesize organometallic compounds on a commercial scale using a one step process where all manipulations are carried out in a single vessel, and which the route to the organometallic compounds does not require the isolation of an intermediate complex.

SUMMARY OF THE INVENTION

This invention relates in part to a one pot method for large scale production of an organometallic compound comprising (i) reacting a hydrocarbon or heteroatom-containing material with a base material in the presence of a solvent and under reaction conditions sufficient to produce a first reaction mixture comprising a hydrocarbon or heteroatom-containing compound, (ii) adding a metal source compound to said first reaction mixture, (iii) reacting said hydrocarbon or heteroatom-containing compound with said metal source compound under reaction conditions sufficient to produce a second reaction mixture comprising said organometallic compound, and (iv) separating said organometallic compound from said second reaction mixture. This invention also relates in part to a process for producing a film, coating or powder by decomposing an organometallic compound precursor, thereby producing the film, coating or powder. This invention further relates to certain hydrocarbon or heteroatom-containing compounds and organometallic compounds.

The invention has several advantages. For example, the method of the invention is useful in generating organometallic compound precursors that have varied chemical structures and physical properties. The method can be employed to produce organometallic compounds, such as, for instance, transition metal-containing amides, alkoxides, diketonates, cyclopentadienides, imides and the like. The method of the invention is particularly well-suited for large scale production since it can be conducted using the same equipment, some of the same reagents and process parameters that can easily be adapted to manufacture a wide range of products. The method provides for the synthesis of organometallic compounds using a unique process where all manipulations are carried out in a single vessel, and which route to the organometallic compounds does not require the isolation of an intermediate complex.

The method of this invention enables the production of multi-kilogram lots of high purity organometallic compound precursors, e.g., hafnium amide, useful in thin film deposition. Currently such materials are prepared at laboratory scale (<50 grams) in glove boxes to safely handle air and moisture sensitive materials. The method of this invention produces a key, solid, raw material in-situ from liquid components. An in-line filtration or decantation step may be utilized to produce an easily distillable solution, thus minimizing exposure of moisture sensitive mixtures. The chemical vapor deposition/atomic layer deposition organometallic precursors may be utilized to form films as the first next generation high K materials to replace silicon dioxide at and/or beyond the 65 nm technology node.

DETAILED DESCRIPTION OF THE INVENTION

As used herein, "large scale production of an organometallic compound" means production in amounts of about 0.25 kilograms or greater, preferably about 0.5 kilograms or greater, and more preferably about 1.0 kilogram or greater, e.g., multi-kilograms.

As indicated herein, this invention involves a one pot method for large scale production of an organometallic compound comprising (i) reacting a hydrocarbon or heteroatom-containing material with a base material in the presence of a solvent and under reaction conditions sufficient to produce a first reaction mixture comprising a hydrocarbon or heteroatom-containing compound, (ii) adding a metal source compound to said first reaction mixture, (iii) reacting said hydrocarbon or heteroatom-containing compound with said metal source compound under reaction conditions sufficient to produce a second reaction mixture comprising said organometallic compound, and (iv) separating said organometallic compound from said second reaction mixture. The method is particularly well-suited for large scale production since it can be conducted using the same equipment, some of the same reagents and process parameters that can easily be adapted to manufacture a wide range of products. The method provides for the synthesis of organometallic compounds using a unique process where all manipulations are carried out in a single vessel, and which route to the organometallic compounds does not require the isolation of an intermediate complex.

The overall advantage of the method of this invention is a simpler process that utilizes less expensive materials and allows for larger batch sizes. These factors translate to an economic advantage.

With no loss in yield compared to prior art methods, this method of this invention avoids labor-intensive and waste generating material manipulations. This method of this invention also eliminates the formation and isolation of a intermediate, as well as reducing the amount of materials (e.g., chemical reagents, glassware) required substantially. Furthermore, because all transformations occur in one vessel until the final product is isolated, all compounds (e.g., side-products) are confined to one location. The product yield can range from about 75 to 99% or greater, preferably from about 80 to 99% or greater, and more preferably from about 85 to 99% or greater.

The hydrocarbon or heteroatom-containing starting material may be selected from a wide variety of compounds known in the art. Illustrative hydrocarbon or heteroatom-containing compounds include, for example, amines, alcohols, diketones, cyclopentadienes, imines, hydrocarbons, halogens and the like. Preferred hydrocarbon or heteroatom-containing starting materials include amines having the formula HNRR' wherein R and R' are independently methyl, ethyl, propyl, butyl, isopropyl, tert-butyl and the like. Other amines that may be useful in the method of this invention include those having the formulae HNRR', $H_2NR$ and $NH_3$ wherein R and R' are independently a saturated or unsaturated, branched or unbranched, hydrocarbon chain or a ring consisting of less than about 20 carbon atoms, alkyl halide, silane, ether, thioether, ester, thioester, amide, amine, nitrile, ketone or mixtures of the above groups.

The concentration of the hydrocarbon or heteroatom-containing starting material can vary over a wide range, and need only be that minimum amount necessary to react with the base starting material. In general, depending on the size of the first reaction mixture, hydrocarbon or heteroatom-containing starting material concentrations in the range of from about 1 millimole or less to about 1000 millimoles or greater, should be sufficient for most processes.

The base starting material may be selected from a wide variety of compounds known in the art. Illustrative bases include any base with a pKa greater than about 10, preferably greater than about 20, and more preferably greater than about 25. The base material is preferably n-BuLi, t-BuLi, MeLi, NaH, CaH, lithium amides and the like.

The concentration of the base starting material can vary over a wide range, and need only be that minimum amount necessary to react with the hydrocarbon or heteroatom-containing starting material. In general, depending on the size of the first reaction mixture, base starting material concentrations in the range of from about 1 millimole or less to about 1000 millimoles or greater, should be sufficient for most processes.

For the method described herein, an important feature concerns generating the hydrocarbon or heteroatom-containing compound in situ, for example, lithiated amides, alkoxides, diketonates, cyclopentadienides, imides and the like. Generating the hydrocarbon or heteroatom-containing compound in situ in the reaction vessel immediately prior to reaction with the metal source compound is beneficial from a purity standpoint by eliminating the need to isolate and handle any reactive solids. It is also less expensive. Although utilizing hexanes (instead of the more commonly used, within the prior art, aromatic hydrocarbon derivatives) as a solvent slightly lowers the amount of hydrocarbon or heteroatom-containing compound, e.g., amide, in solution, it does allow for easier solvent removal and lowers the risk of solvent impurities remaining in the final product. In an embodiment of this invention, it has been found that for certain less soluble derivatives, for example, the less soluble dimethylamide derivative, a 'spiking' can be performed with a small amount (~5%) of another solvent (e.g., THF) which can increase reactant solubility if desired.

With the high purity in situ generated hydrocarbon or heteroatom-containing compound in place, addition of the metal source compound, e.g., hafnium chloride, can be performed through solid addition, or in some cases more conveniently as a solvent (e.g., hexanes) slurry. Although certain metal source compounds are moisture sensitive and are used under an inert atmosphere such as nitrogen, it is generally to a much lower degree than the hydrocarbon or heteroatom-containing compounds, for example, lithiated amides, alkoxides, diketonates, cyclopentadienides, imides and the like. Furthermore, many metal source compounds such as $HfCl_4$ are denser and easier to transfer.

The hydrocarbon or heteroatom-containing compounds prepared from the reaction of the hydrocarbon or heteroatom-containing starting material and the base starting material may be selected from a wide variety of compounds known in the art. Illustrative hydrocarbon or heteroatom-containing compounds include, for example, lithiated amides, alkoxides, diketonates, cyclopentadienides, imides and the like.

The concentration of the hydrocarbon or heteroatom-containing compounds can vary over a wide range, and need only be that minimum amount necessary to react with the metal source compounds to give the organometallic compounds of this invention. In general, depending on the size of the second reaction mixture, hydrocarbon or heteroatom-containing compound concentrations in the range of from about 1 millimole or less to about 1000 millimoles or greater, should be sufficient for most processes.

The solvent employed in the method of this invention may be any saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, nitrites, silicone oils, other aprotic solvents, or mixtures of one or more of the above; more preferably, diethylether, pentanes, or dimethoxyethanes; and most preferably hexanes or THF. Any suitable solvent which does not unduly adversely interfere with the intended reaction can be employed. Mixtures of one or more different solvents may be employed if desired. The amount of solvent employed is not critical to the subject invention and need only be that amount sufficient to solubilize the reaction components in the reaction mixture. In general, the amount of solvent may range from about 5 percent by weight up to about 99 percent by weight or more based on the total weight of the reaction mixture starting materials.

Reaction conditions for the reaction of the base starting material with the hydrocarbon or heteroatom-containing material, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 80° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps.

The metal source compound may be selected from a wide variety of metal-containing compounds known in the art. Illustrative metals include hafnium, zirconium, titanium, tantalum, molybdenum and other transition metals. The metal source compound is preferably a transition metal halide compound, more preferably $MX_n$ (where M is a transition metal, X is halide and n is a value of 3, 4 or 5) including $HfCl_4$, $HfF_4$, $HfBr_4$, $HfI_4$, $Hf(OTf)_4$ and the like, and most preferably $HfCl_4$. Other metal source compounds may include hafnium metal, $HfOCl_2$ and the like.

The concentration of the metal source compound can vary over a wide range, and need only be that minimum amount necessary to provide the given metal concentration desired to be employed and which will furnish the basis for at least the amount of metal necessary for the organometallic compounds of this invention. In general, depending on the size of the first reaction mixture, metal source compound concentrations in the range of from about 1 millimole or less to about 1000 millimoles or greater, should be sufficient for most processes.

Reaction conditions for the reaction of the hydrocarbon or heteroatom-containing compound with the metal source compound, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 80° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps. Since the method of this invention is carried out in a single pot, the hydrocarbon or heteroatom-containing compound is not separated from the first reaction mixture prior to reacting with the metal source compound. In a preferred embodiment, the metal source compound is added to the first reaction mixture at ambient temperature or at a temperature greater than ambient temperature.

The organometallic compounds prepared from the reaction of the hydrocarbon or heteroatom-containing compound and the metal source compound may be selected from a wide variety of compounds known in the art. For purposes of this invention, organometallic compounds include compounds having a metal-carbon atom bond as well as compounds having a metal-heteroatom bond. Illustrative organometallic compounds include, for example, transition metal-containing amides (e.g., hafnium amides), alkoxides (e.g., hafnium (IV) tert-butoxide), diketonates (e.g., hafnium (IV) acetylacetonate), cyclopentadienides, bis(cyclopentadienyl) hafnium dichloride), imides (e.g., t-butylimidobis(dimethylamino)hafnium) and the like.

The method of this invention provides for the elimination of a glove box filtration. To avoid the use of a glove box, which makes scale up difficult, an in line filtration may be utilized which pumps out the product solution leaving the undesired solids behind. An air-free bag filter may also be used. Alternatively, the solids may be allowed to settle and the supernatant can be removed without the need for a filtration. Solvent washings may be utilized to minimize any product loss due to transfer. Another, yet less preferred, method would simply entail removing all the contents, including solids, and distilling, or simply distilling directly from the reaction pot (however this process causes distillation to be less efficient).

Once the relatively solid-free solution has been transferred to the distillation flask, the product may be distilled quite easily away from the reaction solvent and any undesired byproducts. Due to the fact that the method of this invention is performed outside a glovebox, the reaction can be readily scaled to kilogram levels.

For organometallic compounds prepared by the method of this invention, purification can occur through recrystallization, more preferably through extraction of reaction residue (e.g., hexane) and chromatography, and most preferably through sublimation and distillation.

Alternative methods included within the scope of this invention include, for example, the utilization of HCl salts of the desired amine, instead of the amine itself, as the amide source, as well as the elimination of the lithiation step by utilizing excess amine to react with the $HfCl_4$ and to tie up the resulting HCl generated as a protonated amine chloride.

Furthermore, this process is not limited to hafnium amide systems. It can also be extended to other metals as well as other anionic ligands. Examples of other metals include, but are not limited to, zirconium, titanium, tantalum, and molybdenum. Other ligands include, but are not limited to, alkoxides, betadiketonates, cyclopentadienides, imides, nitrates, anionic hydrocarbons, halides, carbonates and the like.

Those skilled in the art will recognize that numerous changes may be made to the method described in detail herein, without departing in scope or spirit from the present invention as more particularly defined in the claims below.

Examples of techniques that can be employed to characterize the organometallic compounds formed by the synthetic methods described above include, but are not limited to, analytical gas chromatography, nuclear magnetic resonance, thermogravimetric analysis, inductively coupled plasma mass spectrometry, differential scanning calorimetry, vapor pressure and viscosity measurements.

Relative vapor pressures, or relative volatility, of organometallic compound precursors described above can be measured by thermogravimetric analysis techniques known in the art. Equilibrium vapor pressures also can be measured, for example by evacuating all gases from a sealed vessel, after which vapors of the compounds are introduced to the vessel and the pressure is measured as known in the art.

Many organometallic compound precursors described herein are liquid at room temperature and are well suited for preparing in-situ powders and coatings. For instance, a liquid organometallic compound precursor can be applied to a substrate and then heated to a temperature sufficient to decompose the precursor, thereby forming a metal or metal oxide coating on the substrate. Applying a liquid precursor to the substrate can be by painting, spraying, dipping or by other techniques known in the art. Heating can be conducted in an oven, with a heat gun, by electrically heating the substrate, or by other means, as known in the art. A layered coating can be obtained by applying an organometallic compound precursor, and heating and decomposing it, thereby forming a first layer, followed by at least one other coating with the same or different precursors, and heating.

Liquid organometallic compound precursors such as described above also can be atomized and sprayed onto a substrate. Atomization and spraying means, such as nozzles, nebulizers and others, that can be employed are known in the art.

In preferred embodiments of the invention, an organometallic compound, such as described above, is employed in gas phase deposition techniques for forming powders, films or coatings. The compound can be employed as a single source precursor or can be used together with one or more other precursors, for instance, with vapor generated by heating at least one other organometallic compound or metal complex. More than one organometallic compound precursor, such as described above, also can be employed in a given process.

Deposition can be conducted in the presence of other gas phase components. In an embodiment of the invention, film deposition is conducted in the presence of at least one non-reactive carrier gas. Examples of non-reactive gases include inert gases, e.g., nitrogen, argon, helium, as well as other gases that do not react with the organometallic compound precursor under process conditions. In other embodiments, film deposition is conducted in the presence of at least one reactive gas. Some of the reactive gases that can be employed include but are not limited to hydrazine, oxygen, hydrogen, air, oxygen-enriched air, ozone ($O_3$), nitrous oxide ($N_2O$), water vapor, organic vapors and others. As known in the art, the presence of an oxidizing gas, such as, for example, air, oxygen, oxygen-enriched air, $O_3$, $N_2O$ or a vapor of an oxidizing organic compound, favors the formation of a metal oxide film.

As indicated above, this invention also relates in part to a process for producing a film, coating or powder. The process includes the step of decomposing at least one organometallic compound precursor, thereby producing the film, coating or powder, as further described below.

Deposition processes described herein can be conducted to form a film, powder or coating that includes a single metal or a film, powder or coating that includes a single metal oxide. Mixed films, powders or coatings also can be deposited, for instance mixed metal oxide films. A mixed metal oxide film can be formed, for example, by employing several organometallic precursors, at least one of which being selected from the organometallic compounds described above.

Gas phase film deposition can be conducted to form film layers of a desired thickness, for example, in the range of from about 1 nm to over 1 mm. The precursors described herein are particularly useful for producing thin films, e.g., films having a thickness in the range of from about 10 nm to about 100 nm. Films of hafnium, hafnium oxides, hafnium silicates and hafnium aluminates, for instance, can be considered for fabricating metal electrodes, in particular as n-channel metal electrodes in logic, as capacitor electrodes for DRAM applications, and as dielectric materials.

The process also is suited for preparing layered films, wherein at least two of the layers differ in phase or composition. Examples of layered film include metal-insulator-semiconductor, and metal-insulator-metal.

In an embodiment, the invention is directed to a process that includes the step of decomposing vapor of an organometallic compound precursor described above, thermally, chemically, photochemically or by plasma activation, thereby forming a film on a substrate. For instance, vapor generated by the compound is contacted with a substrate having a temperature sufficient to cause the organometallic compound to decompose and form a film on the substrate.

The organometallic compound precursors can be employed in chemical vapor deposition or, more specifically, in metal organic chemical vapor deposition processes known in the art. For instance, the organometallic compound precursors described above can be used in atmospheric, as well as in low pressure, chemical vapor deposition processes. The compounds can be employed in hot wall chemical vapor deposition, a method in which the entire reaction chamber is heated, as well as in cold or warm wall type chemical vapor deposition, a technique in which only the substrate is being heated.

The organometallic compound precursors described above also can be used in plasma or photo-assisted chemical vapor deposition processes, in which the energy from a plasma or electromagnetic energy, respectively, is used to activate the chemical vapor deposition precursor. The compounds also can be employed in ion-beam, electron-beam assisted chemical vapor deposition processes in which, respectively, an ion beam or electron beam is directed to the substrate to supply energy for decomposing a chemical vapor deposition precursor. Laser-assisted chemical vapor deposition processes, in which laser light is directed to the substrate to affect photolytic reactions of the chemical vapor deposition precursor, also can be used.

The process of the invention can be conducted in various chemical vapor deposition reactors, such as, for instance, hot or cold-wall reactors, plasma-assisted, beam-assisted or laser-assisted reactors, as known in the art.

Examples of substrates that can be coated employing the process of the invention include solid substrates such as metal substrates, e.g., Al, Ni, Ti, Co, Pt, Ta; metal silicides, e.g., $TiSi_2$, $CoSi_2$, $NiSi_2$; semiconductor materials, e.g., Si, SiGe, GaAs, InP, diamond, GaN, SiC; insulators, e.g., $SiO_2$, $Si_3N_4$, $HfO_2$, $Ta_2O_5$, $Al_2O_3$, barium strontium titanate (BST); barrier materials, e.g., TiN, TaN; or on substrates that include combinations of materials. In addition, films or coatings can be formed on glass, ceramics, plastics, thermoset polymeric materials, and on other coatings or film layers. In preferred embodiments, film deposition is on a substrate used in the manufacture or processing of electronic components. In other embodiments, a substrate is employed to support a low resistivity conductor deposit that is stable in the presence of an oxidizer at high temperature or an optically transmitting film.

The process of the invention can be conducted to deposit a film on a substrate that has a smooth, flat surface. In an embodiment, the process is conducted to deposit a film on a substrate used in wafer manufacturing or processing. For instance, the process can be conducted to deposit a film on patterned substrates that include features such as trenches, holes or vias. Furthermore, the process of the invention also can be integrated with other steps in wafer manufacturing or processing, e.g., masking, etching and others.

Chemical vapor deposition films can be deposited to a desired thickness. For example, films formed can be less than 1 micron thick, preferably less than 500 nanometer and more preferably less than 200 nanometer thick. Films that are less than 50 nanometer thick, for instance, films that have a thickness between about 20 and about 30 nanometers, also can be produced.

Organometallic compound precursors described above also can be employed in the process of the invention to form films by atomic layer deposition (ALD) or atomic layer nucleation (ALN) techniques, during which a substrate is exposed to alternate pulses of precursor, oxidizer and inert gas streams. Sequential layer deposition techniques are described, for example, in U.S. Pat. No. 6,287,965 and in U.S. Pat. No. 6,342,277. The disclosures of both patents are incorporated herein by reference in their entirety.

For example, in one ALD cycle, a substrate is exposed, in step-wise manner, to: a) an inert gas; b) inert gas carrying precursor vapor; c) inert gas; and d) oxidizer, alone or together with inert gas. In general, each step can be as short as the equipment will permit (e.g. milliseconds) and as long as the process requires (e.g. several seconds or minutes). The duration of one cycle can be as short as milliseconds and as long as minutes. The cycle is repeated over a period that can range from a few minutes to hours. Film produced can be a few nanometers thin or thicker, e.g., 1 millimeter (mm).

The process of the invention also can be conducted using supercritical fluids. Examples of film deposition methods that use supercritical fluid that are currently known in the art include chemical fluid deposition; supercritical fluid transport-chemical deposition; supercritical fluid chemical deposition; and supercritical immersion deposition.

Chemical fluid deposition processes, for example, are well suited for producing high purity films and for covering complex surfaces and filling of high-aspect-ratio features. Chemical fluid deposition is described, for instance, in U.S. Pat. No. 5,789,027. The use of supercritical fluids to form films also is described in U.S. Pat. No. 6,541,278 B2. The disclosures of these two patents are incorporated herein by reference in their entirety.

In an embodiment of the invention, a heated patterned substrate is exposed to one or more organometallic compound precursors, in the presence of a solvent, such as a near critical or supercritical fluid, e.g., near critical or supercritical $CO_2$. In the case of $CO_2$, the solvent fluid is provided at a pressure above about 1000 psig and a temperature of at least about 30° C.

The precursor is decomposed to form a metal film on the substrate. The reaction also generates organic material from the precursor. The organic material is solubilized by the solvent fluid and easily removed away from the substrate. Metal oxide films also can be formed, for example by using an oxidizing gas.

In an example, the deposition process is conducted in a reaction chamber that houses one or more substrates. The substrates are heated to the desired temperature by heating the entire chamber, for instance, by means of a furnace. Vapor of the organometallic compound can be produced, for example, by applying a vacuum to the chamber. For low boiling compounds, the chamber can be hot enough to cause vaporization of the compound. As the vapor contacts the heated substrate surface, it decomposes and forms a metal or metal oxide film. As described above an organometallic compound precursor can be used alone or in combination with one or more components, such as, for example, other organometallic precursors, inert carrier gases or reactive gases.

In a system that can be used in producing films by the process of the invention, raw materials can be directed to a gas-blending manifold to produce process gas that is supplied to a deposition reactor, where film growth is conducted. Raw materials include, but are not limited to, carrier gases, reactive gases, purge gases, precursor, etch/clean gases, and others. Precise control of the process gas composition is accomplished using mass-flow controllers, valves, pressure transducers, and other means, as known in the art. An exhaust manifold can convey gas exiting the deposition reactor, as well as a bypass stream, to a vacuum pump. An abatement system, downstream of the vacuum pump, can be used to remove any hazardous materials from the exhaust gas. The deposition system can be equipped with in-situ analysis system, including a residual gas analyzer, which permits measurement of the process gas composition. A control and data acquisition system can monitor the various process parameters (e.g., temperature, pressure, flow rate, etc.).

The organometallic compound precursors described above can be employed to produce films that include a single metal or a film that includes a single metal oxide. Mixed films also can be deposited, for instance mixed metal oxide films. Such films are produced, for example, by employing several organometallic precursors. Metal films also can be formed, for example, by using no carrier gas, vapor or other sources of oxygen. Films formed by the methods described herein can be characterized by techniques known in the art, for instance, by X-ray diffraction, Auger spectroscopy, X-ray photoelectron emission spectroscopy, atomic force microscopy, scanning electron microscopy, and other techniques known in the art. Resistivity and thermal stability of the films also can be measured, by methods known in the art.

Various modifications and variations of this invention will be obvious to a worker skilled in the art and it is to be understood that such modifications and variations are to be included within the purview of this application and the spirit and scope of the claims.

COMPARATIVE EXAMPLE A

In a glove box, anhydrous hexanes (3.5 liters) was added to a 5 liter, 3-neck round-bottom flask containing a stir bar. While stirring, $LiNMe_2$ (325 grams, 6.37 mol) was added. Onto the 3-necks were placed a septum (to allow use of a thermocouple), a condenser, and a powder addition funnel charged with $HfCl_4$ (500 grams, 1.56 mol). The $HfCl_4$ was added slowly over 3 hours. More hexanes were added as necessary to keep the mixture stirring. The reaction mixture heated up to between 40-60° C. depending on the rates of addition and stirring. Stirring was continued for 12-16 hours, then the mixture was allowed to settle. The reaction mixture was filtered through a medium-porosity glass frit to remove the colorless solid byproducts and yielded a yellow solution as the filtrate. The solution was concentrated in vacuo. The residue was transferred to a short path still for distillation. Distillation was performed under vacuum (~0.2 torr) at about 60° C. to a receiver flask at 0° C. The product (387 grams, 1.09 mol) was collected as a colorless to off-white solid at 0° C. or a pale yellow liquid at 30° C. Yield: 70%.

The compound tetrakis(dimethylamino)hafnium, an off-white solid, has been reported and characterized by NMR previously (note we report mp=28° C.). Purity for this compound was measured by $^1H$ NMR (>99%), TGA (>99.5%), and ICP-MS (>99.8% (Zr included)).

EXAMPLE 1

A hexane solution of 0.91 M "BuLi (3.6 L, 3.3 mol) was added to a 5 L, 3 neck round-bottom flask blanketed with a nitrogen purge and equipped with a mechanical stirrer, a water condenser, and a thermocouple. The flask was cooled in a bath to −20° C. With stirring, ethylmethylamine (205 grams, 3.5 mol) was added slowly by cannula at a rate such that the reaction mixture temperature was kept under 10° C. After the addition was complete (~2 hours), the reaction mixture was allowed to warm slowly to 20° C. and stirring was continued overnight (~16 hours). Anhydrous inhibitor-free THF (0.2 L) was added to the white suspension. A solid addition funnel containing $HfCl_4$ (250.1 gram, 0.78 mol) was attached to the reaction flask under a heavy purge. The $HfCl_4$ was added slowly (~2 hours), and the observed exothermic response registered a maximum temperature of 45° C. After the addition, the mixture was allowed to stir for 4 days (note: other examples have shown a stir time of 16 hours is adequate). Stirring was discontinued and the solids were allowed to settle. The reaction was filtered through a medium porosity frit in a glove box. The solution was concentrated down to approximately 350 mL under reduced pressure. The concentrated solution was then transferred to a vacuum distillation apparatus and purified by distillation (bp=80° C. at 0.5 torr). The product (262 grams, 0.638 mol) was obtained as a clear, slightly pale-yellow liquid. Yield: 82%.

Stepwise Procedure:
1. Dry glassware
2. Add 3.6 L of 0.91 M ″BuLi hexane solution to 5 L,
3. neck round bottom flask under nitrogen
3. Cool flask to −20° C.
4. With mechanical stirring, slowly add 205 grams of ethylmethylamine by cannula
5. Keep reaction temperature at or below 10° C. during addition
6. Stir overnight (~16 hours) allowing flask to warm to room temperature (~20° C.)
7. Add THF
8. Add 250 grams of $HfCl_4$ slowly (~2 hours)
9. Stir 4 days (note: in other examples, one day has been shown to be sufficient)
10. Filter reaction under inert atmosphere[a]
11. Concentrate filtrate to ~350 mL
12. Transfer filtrate to a vacuum distillation apparatus
13. Distill product in vacuo (bp=80° C. at 0.5 torr)[a]

[a]Solid residue will react with air and moisture. It should be quenched slowly with 2-propanol/hexanes under nitrogen, then water before disposing of in a proper chemical waste receptacle The compound tetrakis(ethylmethylamino)hafnium is a slightly pale-yellow liquid (mp=<−50° C., d=1.3 g/mL at 22° C.). $^1H$ NMR (400 MHz, toluene-$d_8$, 20° C., δ): 3.27 (8H, q, J=7 Hz, $CH_2CH_3$), 2.99 (12H, s, methyl), 1.16 (12H, t, J=7 Hz, $CH_2CH_3$). Purity for this compound was measured by $^1H$ NMR (>99%), TGA (>99.5%), and ICP-MS (>99.8% (Zr included)).

EXAMPLE 2

A dry, jacketed (coolant-filled with circulating chiller) 20 L reactor, equipped with a mechanical stirrer, condenser (outlet to scrubber for amine vapors), thermocouple, nitrogen inlet, and reagent entry lines, was cooled to −20° C. Anhydrous nitrogen-purged hexanes (5 L) were added, followed by the addition of anhydrous nitrogen-purged diethylamine (1.34 L, 12.95 mol). While maintaining a reaction temperature below 10° C., a 2.5M solution of ″BuLi (4.7 L, 11.77 mol) was added via line transfer. After the addition was completed, the reactor was allowed to warm to ambient temperature (~22° C.), then stirred for an additional 1 hour. $HfCl_4$ (807 grams, 2.52 mol) was added over ~3 hours as a slurry (hexanes, 3 L) via a stainless steel line. The reaction mixture was stirred for 16 hours (convenient to stir overnight), after which time the stirring was stopped and the solids were allowed to settle. The supernatant was transferred via line transfer to a distillation apparatus. The remaining solids were stirred with additional hexanes (2×2 L), drawing off the supernatant as before once stirring was stopped and the solids had settled. The hexanes were removed by distillation, followed by vacuum distillation of the product (bp=0.5 torr at 110° C.). Yield 80-90% (85%=1 kg $Hf(NEt_2)_4$). The reactor was rinsed with four solvents in series, namely isopropanol, deionized water, isopropanol, and hexanes, before being dried thoroughly with a nitrogen purge.

Stepwise Procedure:
1. Dry and set up reactor
2. Set jacket temperature to −20° C.
3. Add 5 L of hexanes
4. Add 1.34 L diethylamine
5. After the reaction mixture is at −20° C., slowly add (with stirring) 4.7 L of 2.5 M ″BuLi in hexanes via line transfer, keeping reaction temperature below 10° C.
6. After addition is complete, allow reactor to warm to room temperature (~20° C.).
7. Stir for an additional hour
8. Add 807 grams $HfCl_4$ slowly (~3 hours) as a slurry in hexanes
9. Stir 16 hours
10. Stop stirring and allow solids to settle
11. Transfer supernatant to distillation apparatus
12. Wash solids with 4 L of hexanes, allow solids to resettle, and transfer supernatant as before
13. Remove hexanes by distillation
14. Isolate product by vacuum distillation (bp=0.5 torr at 110° C.)
15. Under nitrogen, slowly add 2-propanol/hexanes to remaining solids in reactor to quench any reactive materials
16. Once quenched, slowly add deionized water, and then rinse solids from reactor through reactor outlet
17. Rinse reactor with 2-propanol, then hexanes
18. Dry reactor thoroughly with a nitrogen purge before next use.

The invention claimed is:

1. A one pot method for large scale production of an organometallic compound comprising a transition metal-containing amide, a transition metal-containing alkoxide, a transition metal-containing diketonate or a transition metal-containing imide, said one pot method comprising (i) reacting a hydrocarbon or heteroatom-containing material with a base material in the presence of a solvent and under reaction conditions sufficient to produce a first reaction mixture comprising a hydrocarbon or heteroatom-containing compound, (ii) adding a transition metal source compound to said first reaction mixture, (iii) reacting said hydrocarbon or heteroatom-containing compound with said transition metal source compound under reaction conditions sufficient to produce a second reaction mixture comprising said organometallic compound, and (iv) separating said organometallic compound from said second reaction mixture.

2. The one pot method of claim 1 wherein the large scale production amounts to about 0.25 kilograms of said organometallic compound.

3. The one pot method of claim 1 wherein the large scale production amounts to about 0.5 kilograms of said organometallic compound.

4. The one pot method of claim 1 wherein the large scale production amounts to about 1.0 kilograms of said organometallic compound.

5. The one pot method of claim 1 wherein the organometallic compound yield is from about 75 to 99%.

6. The one pot method of claim 1 wherein the organometallic compound yield is from about 80 to 99%.

7. The one pot method of claim 1 wherein the hydrocarbon or heteroatom-containing material comprises an amine, alcohol, diketone, imine, hydrocarbon or halogen.

8. The one pot method of claim 1 wherein the base material has a pKa greater than about 10.

9. The one pot method of claim 1 wherein the base material comprises BuLi, MeLi, NaH, CaH or a lithium amide.

10. The one pot method of claim 1 wherein the hydrocarbon or heteroatom-containing compound comprises a lithiated amide, a lithiated alkoxide, a lithiated diketonate or a lithiated imide.

11. The one pot method of claim 1 wherein the transition metal source compound is represented by the formula $MX_n$ wherein M is a transition metal, X is halide and n is a value of 3.4 or 5.

12. The one pot method of claim 11 wherein the transition metal is selected from hafnium, titanium, zirconium, tantalum and molybdenum.

13. The one pot method of claim 1 wherein the transition metal source compound comprises $HfCl_4$, $HfF_4$, $HfBr_4$, $HfI_4$ or $Hf(OTf)_4$.

14. The one pot method of claim 1 wherein the transition metal source compound is $HfCl_4$.

15. The one pot method of claim 1 wherein the transition metal source compound is added to the first reaction mixture at ambient temperature or at a temperature greater than ambient temperature.

16. The one pot method of claim 1 wherein the solvent is selected from saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, nitriles, silicone oils, other aprotic solvents, or mixtures of one or more of the above.

17. The one pot method of claim 1 wherein the solvent is selected from hexanes, THF or mixtures thereof.

18. The one pot method of claim 1 wherein the organometallic compound comprises hafnium amide, hafnium (IV) tert-butoxide, hafnium (TV) acetylacetonate, or t-butylimidobis(dimethylamino)hafnium.

19. A one pot method for producing a hafnium amide compound comprising (i) reacting an amine with a lithiated base material to produce a first reaction mixture comprising a lithium amide, (ii) adding a hafnium halide to said first reaction mixture, (iii) reacting said lithium amide with said hafnium halide under reaction conditions sufficient to produce a second reaction mixture comprising said hafnium amide compound, and (iv) separating said hafnium amide compound from said second reaction mixture.

20. A one pot method for large scale production of an organometallic compound comprising a transition metal-containing amide, a transition metal-containing alkoxide, a transition metal-containing diketonate, a transition metal-containing cyclopentadienide or a transition metal-containing imide, said one pot method comprising (i) reacting a hydrocarbon or heteroatom-containing material with a base material in the presence of a solvent and under reaction conditions sufficient to produce a first reaction mixture comprising a hydrocarbon or heteroatom-containing compound, (ii) adding a transition metal source compound to said first reaction mixture, wherein said transition metal source compound is added to said first reaction mixture at ambient temperature or at a temperature greater than ambient temperature, (iii) reacting said hydrocarbon or heteroatom-containing compound with said transition metal source compound under reaction conditions sufficient to produce a second reaction mixture comprising said organometallic compound, and (iv) separating said organometallic compound from said second reaction mixture.

21. A one pot method for large scale production of an organometallic compound comprising a transition metal-containing amid, a transition metal-containing alkoxide, a transition metal-containing diketonate, a transition metal-containing cyclopentadienide or a transition metal-containing imide, said one pot method comprising (i) reacting a hydrocarbon or heteroatom-containing material with a base material in the presence of a solvent and under reaction conditions sufficient to produce a first reaction mixture comprising a hydrocarbon or heteroatom-containing compound, (ii) adding a transition metal source compound to said first reaction mixture, (iii) reacting said hydrocarbon or heteroatom-containing compound with said transition metal source compound under reaction conditions sufficient to produce a second reaction mixture comprising said organometallic compound, and (iv) separating said organometallic compound from said second reaction mixture; wherein the organometallic compound yield is from about 80 to 99%.

22. A one pot method for large scale production of an organometallic compound comprising (i) reacting a hydrocarbon or heteroatom-containing material with a base material in the presence of a solvent and under reaction conditions sufficient to produce a first reaction mixture comprising a hydrocarbon or heteroatom-containing compound, wherein said solvent is selected from hexanes, THF or mixtures thereof, (ii) adding a metal source compound to said first reaction mixture, (iii) reacting said hydrocarbon or heteroatom-containing compound with said metal source compound under reaction conditions sufficient to produce a second reaction mixture comprising said organometallic compound, and (iv) separating said organometallic compound tram said second reaction mixture.

23. The one pot method of claim 20 wherein the large scale production amounts to about 0.25 kilograms of said organometallic compound.

24. The one pot method of claim 20 wherein the large scale production amounts to about 0.5 kilograms of said organometallic compound.

25. The one pot method of claim 20 wherein the large scale production amounts to about 1.0 kilograms of said organometallic compound.

26. The one pot method of claim 20 wherein the organometallic compound yield is from about 75 to 99%.

27. The one pot method of claim 20 wherein the organometallic compound yield is from about 80 to 99%.

28. The one pat method of claim 20 wherein the hydrocarbon or heteroatom-containing material comprises an amine, alcohol, diketone, cyclopentadiene, imine, hydrocarbon or halogen.

29. The one pot method of claim 20 wherein the base material has a pKa greater than about 10.

30. The one pot method of claim 20 wherein the base material comprises BuLi, MeLi, NaH, CaH or a lithium amide.

31. The one pot method of claim 20 wherein the hydrocarbon or heteroatom-containing compound comprises a lithiated amide, a lithiated alkoxide, a lithiated diketonate, lithiated cyclopentadienide or a lithiated imide.

32. The one pot method of claim 20 wherein the transition metal source compound is represented by the formula $MX_n$ wherein M is a transition metal, X is halide and n is a value of 3, 4 or 5.

33. The one pot method of claim 32 wherein the transition metal is selected from hafnium, titanium, zirconium, tantalum and molybdenum.

34. The one pot method of claim 20 wherein the transition metal source compound comprises $HfCl_4$, $HfF_4$, $HfBr_4$, $HfI_4$ or $Hf(OTf)_4$.

35. The one pot method of claim 20 wherein the solvent is selected from saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, nitriles, silicone oils, other aprotic solvents, or mixtures of one or more of the above.

36. The one pot method of claim 20 wherein the organometallic compound comprises hafnium amide, hafnium (IV) tert-butoxide, hafnium (IV) aetylacetonate, bis(cyclopentadienyl)hafnium dichloride or t-butylimidobis(dimethylamino)hafnium.

37. The one pot method of claim 21 wherein the large scale production amounts to about 0.25 kilograms of said organometallic compound.

38. The one pot method of claim 21 wherein the large scale production amounts to about 0.5 kilograms of said organometallic compound.

39. The one pot method of claim 21 wherein the large scale production amounts to about 1.0 kilograms of said organometallic compound.

40. The one pot method of claim 21 wherein the hydrocarbon or heteroatom-containing material comprises an amine, alcohol, diketone, cyclopentadiene, imine, hydrocarbon or halogen.

41. The one pot method of claim 21 wherein the base material has a pKa greater than about 10.

42. The one pot method of claim 21 wherein the base material comprises BuLi, MeLi, NaH, CaH or a lithium amide.

43. The one pot method of claim 21 wherein the hydrocarbon or heteroatom-containing compound comprises a lithiated amide, a lithiated alkoxide, a lithiated diketonate, lithiated cyclopentadienide or a lithiated imide.

44. The one pot method of claim 21 wherein the transition metal source compound is represented by the formula $MX_n$ wherein M is a transition metal, X is halide and n is a value of 3, 4 or 5.

45. The one pot method of claim 44 wherein the transition metal is selected from hafnium, titanium, zirconium, tantalum and molybdenum.

46. The one pot method of claim 21 wherein the transition metal source compound comprises $HfCl_4$, $HfF_4$, $HfBr_4$, $HfI_4$ or $Hf(OTf)_4$.

47. The one pot method of claim 21 wherein the transition metal source compound is added to the first reaction mixture at ambient temperature or at a temperature greater than ambient temperature.

48. The one pot method of claim 21 wherein the solvent is selected from saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, nitriles, silicone oils, other aprotic solvents, or mixtures of one or more of the above.

49. The one pot method of claim 21 wherein the organometallic compound comprises hafnium amide, hafnium (IV) tert-butoxide, hafnium (IV) acetylacetonate, bis(cyclopentadienyl)hafnium dichloride or t-butylimidobis(dimethylamino)hafnium.

50. The one pot method of claim 22 wherein the large scale production amounts to about 0.25 kilograms of said organometallic compound.

51. The one pot method of claim 22 wherein the large scale production amounts to about 0.5 kilograms of said organometallic compound.

52. The one pot method of claim 22 wherein the large scale production amounts to about 1.0 kilograms of said organometallic compound.

53. The one pot method of claim 22 wherein the organometallic compound yield is from about 75 to 99%.

54. The one pot method of claim 22 wherein the organometallic compound yield is from about 80 to 99%.

55. The one pot method of claim 22 wherein the hydrocarbon or heteroatom-containing material comprises an amine, alcohol, diketone, cyclopentadiene, imine, hydrocarbon or halogen.

56. The one pot method of claim 22 wherein the base material has a pKa greater than about 10.

57. The one pot method of claim 22 wherein the base material comprises BuLi, MeLi NaH, CaH or a lithium amide.

58. The one pot method of claim 22 wherein the hydrocarbon or heteroatom-containing compound comprises a lithiated amide, a lithiated alkoxide, a lithiated diketonate, lithiated cyclopentadienide or a lithiated imide.

59. The one pot method of claim 22 wherein the transition metal source compound is represented by the formula $MX_n$ wherein M is a transition metal, X is halide and a is a value of 3, 4 or 5.

60. The one pot method of claim 59 wherein the transition metal is selected from hafnium, titanium, zirconium, tantalum and molybdenum.

61. The one pot method of claim 22 wherein the transition metal source compound comprises $HfCl_4$, $HfF_4$, $HfBr_4$, $HfI_4$, or $Hf(OTf)_4$.

62. The one pot method of claim 22 wherein the transition metal source compound is added to the first reaction mixture at ambient temperature or at a temperature greater than ambient temperature.

63. The one pot method of claim 22 wherein the organometallic compound comprises hafnium amide, hafnium (IV) tert-butoxide, hafnium (IV) acetylacetonate, bis(cyclopentadienyl)hafnium dichloride or t-butylimidobis(dimethylamino)hafnium.

* * * * *